(12) United States Patent
Goldmann et al.

(10) Patent No.: US 8,236,797 B2
(45) Date of Patent: Aug. 7, 2012

(54) BROMO-PHENYL SUBSTITUTED THIAZOLYL DIHYDROPYRIMIDINES

(75) Inventors: Siegfried Goldmann, Wuppertal (DE); Jing Li, Dongguan (CN); Yi Song Liu, Dongguan (CN)

(73) Assignee: Sunshine Lake Pharma Co., Ltd., Dongguan, Guangdong (CN)

( * ) Notice: Subject to any disclaimer, the term of this patent is extended or adjusted under 35 U.S.C. 154(b) by 189 days.

(21) Appl. No.: 12/664,392

(22) PCT Filed: Jun. 18, 2008

(86) PCT No.: PCT/CN2008/001187
§ 371 (c)(1),
(2), (4) Date: May 19, 2010

(87) PCT Pub. No.: WO2008/154817
PCT Pub. Date: Dec. 24, 2008

(65) Prior Publication Data
US 2010/0240655 A1   Sep. 23, 2010

(30) Foreign Application Priority Data
Jun. 18, 2007   (CN) .......................... 2007 1 0119019

(51) Int. Cl.
*A61K 31/535*   (2006.01)
*C07D 413/14*   (2006.01)
(52) U.S. Cl. ..................................... 514/235.2; 544/122
(58) Field of Classification Search .................. 544/122; 514/235.8
See application file for complete search history.

(56) References Cited

U.S. PATENT DOCUMENTS

| | | | |
|---|---|---|---|
| 4,822,798 | A | 4/1989 | Stoltefuss et al. |
| 6,436,943 | B1 | 8/2002 | Stoltefuss et al. |
| 6,503,913 | B1 | 1/2003 | Goldmann et al. |
| 6,696,451 | B1 | 2/2004 | Stoltefuss et al. |
| 7,074,784 | B2 | 7/2006 | Goldmann et al. |
| 2010/0004268 | A1 | 1/2010 | Li et al. |
| 2010/0010013 | A1 | 1/2010 | Li et al. |

FOREIGN PATENT DOCUMENTS

| | | |
|---|---|---|
| WO | WO-0058302 | 5/2000 |
| WO | WO-0145712 | 6/2001 |
| WO | WO-0168639 | 9/2001 |
| WO | WO-0168641 | 9/2001 |
| WO | WO-0168642 | 9/2001 |
| WO | WO-0168647 | 9/2001 |
| WO | WO-2008009209 | 1/2008 |
| WO | WO-2008154818 | 12/2008 |
| WO | WO-2008154819 | 12/2008 |
| WO | WO-2008154820 | 12/2008 |

OTHER PUBLICATIONS

Huf, Joel R., "HIV Protease: A Novel Chemotherapeutic Target for AIDS," Journal of Medicinal Chemistry, Aug. 1991, pp. 2305-2314, vol. 34, No. 8.*

* cited by examiner

*Primary Examiner* — Rebecca Anderson
(74) *Attorney, Agent, or Firm* — Kam W. Law; Squire Sanders

(57) ABSTRACT

This invention relates to a bromo-phenyl substituted thiazolyl dihydropyrimidine, its preparation method and use as a medicament for treating and preventing hepatitis B infections. The invention also relates to a composition comprising the dihydropyrimidine, one or more antiviral agents and, optionally, an immunomodulator for treating and preventing HBV infections.

22 Claims, No Drawings

BROMO-PHENYL SUBSTITUTED THIAZOLYL DIHYDROPYRIMIDINES

This is a U.S. national stage application of the International Patent Application No. PCT/CN2008/001187, filed Jun. 18, 2008, which claims priority to Chinese Patent Application No. 200710119019.8, filed Jun. 18, 2007, both of which are incorporated herein by reference in their entirety.

FIELD OF THE INVENTION

The invention relates to a new bromo-phenyl substituted thiazolyl dihydropyrimidine, its preparation method and use as a medicament especially for treating and preventing hepatitis B infections. The invention also relates to a composition comprising the dihydropyrimidine, other antiviral agent and, when appropriate, an immunomodulator and a medicament comprising the composition especially for treating and preventing HBV infections such as hepatitis B infections.

BACKGROUND OF THE INVENTION

The hepatitis B virus belongs to the family of hepadna viruses. It can cause acute and/or persistent or progressive chronic diseases. Many other clinical manifestations in the pathological state are also caused by the hepatitis B virus—in particular chronic inflammation of the liver, cirrhosis of the liver and hepatocellular carcinoma. In addition, coinfection with the hepatitis delta virus may have adverse effects on the progress of the disease.

The interferon and lamivudine are conventional medicaments approved to be used for treating chronic hepatitis. However, the interferon has just moderate activity but has an adverse side reaction. Although lamivudine has good activity, its resistance develops rapidly during the treatment and relapse effects often appear after the treatment is stopped. The $IC_{50}$ value of lamivudine (3-TC) is 300 nM (Science, 299 (2003), 893-896).

U.S. Pat. No. 7,074,784 discloses 6-amidoalkyldihydropyrimidine and its use as a medicament especially for treating and preventing hepatitis B infection.

It is described in Example 12 of U.S. Pat. No. 7,074,784 that $R^1$ is o-chlorine, $R^2$ is p-chlorine, $R^6$ is 3,5-difluoro-pyridin-2-yl, X is —$CH_2$— and Z is morpholinyl. The compound can inhibit the growth of hepatitis B virus during cell culturing. The $IC_{50}$ value is 2 nM (tested by themselves).

The main substitution in Example 12 is replacing bis-chlorine with $R^1$ (o-bromine) and $R^2$ (p-fluorine), which results in the $IC_{50}$ of Compound 9 being 7 nM (described in Example 9 of the patent). And when the main substituents are changed into $R^1$ (o-chlorine) and $R^2$ (p-fluorine), an approximate $IC_{50}$ value is also obtained ($IC_{50}$=2-4 nM in Example 5).

It is indicated that the $IC_{50}$ value cannot increase with the variation of the main substituents $R^1$ and $R^2$ (see Table 1).

U.S. Pat. No. 7,074,784 B2 also discloses an example, wherein a difluoro residue is substituted for thiazol-2-yl (described in Example 45 of the patent). The derivative has a similar $IC_{50}$ value (2 nM) (see Table 1).

TABLE 1

Example 2 of U.S. Pat. No. 7,074,784 B2

| Example | $R^1$ | $R^2$ | $R^3$ | $R^6$ | $IC_{50}$ (nM) |
|---------|------|------|------|------|----------------|
| 12 | Cl | Cl | $CH_3$ | 3,5-difluoropyridin-2-yl | 2 (self-tested) |
| 9 | Br | F | $CH_3$ | 3,5-difluoropyridin-2-yl | 7 |
| 5 | Cl | F | $CH_3$ | 3,5-difluoropyridin-2-yl | 2-4 |
| 45 | Cl | Cl | $CH_3$ | 2-methylthiazol-2-yl | 2 |

DETAILED DESCRIPTION OF THE INVENTION

We have surprisingly discovered that a derivative with an activity of 10 times higher and the $IC_{50}$ value of less than 1 nM can be obtained by substituting with thiazol-2-yl and changing the main substituents into $R^1$=o-bromine and $R^2$=p-fluorine. This is unexpected when reading U.S. Pat. No. 7,074,784 (see Table 2).

TABLE 2

Some Examples of this Invention

| Example | $R^1$ | $R^2$ | $R^3$ | $R^6$ | $IC_{50}$ (nM) |
|---------|------|------|------|------|----------------|
| 1 | Br | F | $CH_3$ | thiazol-2-yl | 0.3 |
| 2 | Br | Cl | $CH_2CH_3$ | thiazol-2-yl | 0.2 |

This invention relates to a compound having formula (I) and its isomer (Ia),

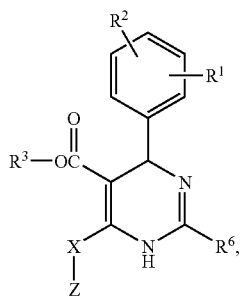
(I)

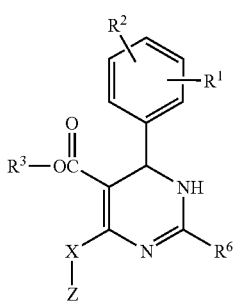
(Ia)

wherein $R^1$ is o-bromine, $R^2$ is p-fluorine, $R^3$ is $C_1$-$C_4$ alkyl, $R^6$ is thiazol-2-yl, X is methylene and Z is morpholinyl.

Preferably, $R^1$ of the compound of the invention having formula (I) and (Ia) is o-bromine, $R^2$ is p-fluorine, $R^3$ is methyl or ethyl, $R^6$ is thiazol-2-yl, X is methylene and Z is morpholinyl.

This invention also relates to an enantiomer of the compound disclosed herein and a mixture thereof. The racemate can be separated by a known method, and fundamentally it is a homogeneous component in a stereoisomer mixture.

The compounds of the invention comprise an isomer having formula (I) and (Ia) and a mixture thereof.

The compound of the invention can also be in a form of a salt, preferably a physiologically acceptable salt.

The physiologically acceptable salt can be an inorganic acid salt or organic acid salt. Preferably it is an inorganic acid salt such as chloride, bromide, phosphate or sulfate, etc., or a carboxylate or a sulfonate, such as acetate, maleate, fumarate, malate, citrate, tartarate, lactate, benzoate or methanesulfonate, ethanesulfonate, benzenesulfonate, toluenesulfonate or naphthalenedisulfonate, etc.

The physiologically acceptable salt can also be a metal salt or an ammonium salt of the compound of the invention. In a preferred example, it is a sodium salt, potassium salt, magnesium salt or calcium salt, and an ammonium salt produced by ammonia or organic amine such as ethylamine, diethylamine or triethylamine, diethanolamine or triethanolamine, dicyclohexylamine, dimethylaminoethyl alcohol, arginine, lysine, ethylenediamine or 2-phenylethylamine, etc.

The compound (I) of the invention can be prepared by the following methods:

[A] firstly a benzaldehyde having formula (II) reacts with a β-ketoester having formula (III) with or without the addition of an alkali or an acid, and, when appropriate, in the presence of an inert organic solvent to produce a benzylidene compound having formula (IV):

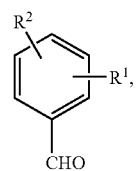
(II)

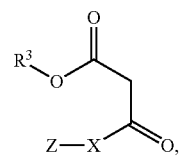
(III)

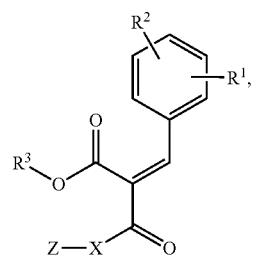
(IV)

wherein $R^1$, $R^2$, $R^3$, X and Z are as defined herein, and then the benzylidene compound reacts with an amidine having formula (V) or a salt thereof (such as hydrochloride or acetate) with or without the addition of an alkali or an acid, and, when appropriate, in the presence of an inert organic solvent:

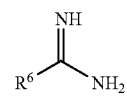
(V)

wherein $R^6$ is as defined herein; or

[B] the β-ketoester having formula (III) reacts with the benzaldehyde having formula (II) and the amidine having formula (V) or a salt thereof (such as hydrochloride or acetate) with or without the addition of an alkali or an acid, and, when appropriate, in the presence of an inert organic solvent in one step; or

[C] if X in formula (I) is methylene, a compound having formula (VI) reacts with morpholine having formula (VII) with or without the addition of an alkali, and, when appropriate, in the presence of an inert organic solvent,

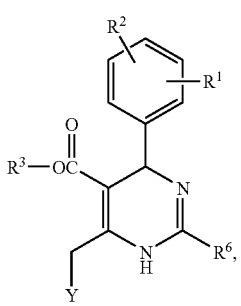
(VI)

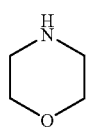
(VII)

wherein $R^1$, $R^2$, $R^3$ and $R^6$ are as defined herein and Y is a nucleophilic substituent, such as chloro, bromo, iodo, methylsulfonyl or toluenesulfonyl; or

[D] the benzaldehyde having formula (II) reacts with a compound having formula (X) and the amidine having formula (V) with or without the addition of an alkali and, when appropriate, in an inert organic solvent,

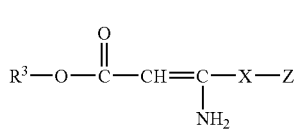
(X)

wherein $R^3$, X and Z are as defined herein.

Compound of formula (VI) can be prepared by, for example, reacting a compound having formula (VIII)

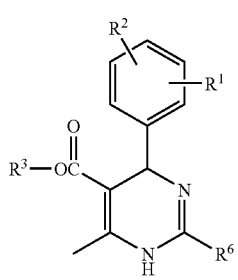
(VIII)

wherein $R^1$, $R^2$, $R^3$ and $R^6$ are as defined herein, with a brominating agent such as N-bromosuccinimide, preferably in an inert organic solution, to produce a compound having formula (IX):

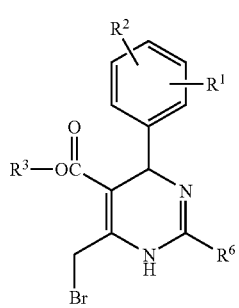
(IX)

and reacting the compound having a nucleophilic substituent, directly or after the compound being further converted according to a conventional method as described in a literature, with the morpholine having formula (VII).

In order to prepare the compound of the invention having formula (I), wherein X is methylene and Z is morpholinyl, a chloroacetate having formula (XI) reacts with morpholine (VII) to produce the β-keto carboxylate of formula (III),

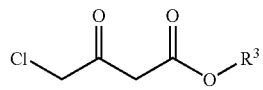
(XI)

wherein $R^3$ is as defined herein.

As a starting material, 2-bromo-4-fluoro-benzaldehyde (II) is commercially available.

As a starting material, β-keto carboxylate (III) is well-known, or can be prepared by known methods published in the literature [for example, D. Baumann, "Umsetzung von Diketen mit Alkoholen, Phenolen und Mercaptanen", in "Methoden der organischen Chemie" (Houben-Weyl), vol. VII/4, 230 ff (1968); Y. Oikawa, K. Sugano und O. Yonemitsu, J. Org. Chem. 43, 2087 (1978)].

The compound (V) is known and can be prepared according to the descriptions of WO-A-99/54326 and WO-A-99/54329.

Morpholine (VII) is commercially available.

Compounds (VIII) and (X) can be prepared according to step [A] or [B] described in WO-A-99/54326.

All inert organic solvents are suitable for use in steps A, B, C and D. The inert organic solvent is preferably an alcohol such as methanol, ethanol and isopropyl alcohol, an ether such as dioxane, diethyl ether, tetrahydrofuran, ethylene glycol monomethyl ether, ethylene glycol dimethyl ether, a carboxylic acid such as acetic acid, dimethylformamide, dimethyl sulfoxide, acetonitrile, pyridine or hexamethyl phosphoric triamide.

The reaction temperature can be varied within quite a wide range. Usually the temperature is between 20° C. and 150° C. Preferably, the temperature is the boiling temperature of the selected solvent.

The reaction can be carried out under the atmospheric pressure or under a high pressure. It is usually carried out under the atmospheric pressure.

The reaction can be carried out with or without an acid or alkali. It is preferable to carry out the reaction in the presence of a weak acid such as acetic acid, formic acid or the like.

An embodiment of the invention relates to a composition comprising A) at least one of the above dihydropyrimidines and B) at least one of other antiviral agents different from A).

A certain embodiment of the invention relates to a composition comprising A) the above dihydropyrimidine, B) an HBV polymerase inhibitor and, when appropriate, C) an immunomodulator.

Preferably the immunomodulator C) is selected from, for example, all the interferons such as α-interferon, β-interferon and γ-interferon, especially α-2a-interferon and α-2b-interferon, an interleukin such as interleukin-2, a polypeptide such as thymosin-α-1 and a thymoctonan, an imidazoquinoline derivative such as levamisole, an immunoglobulin and a therapeutic vaccine.

Thereby, this invention also relates to a composition for treating and preventing HBV infections and its use for treating diseases induced by HBV.

The use of the combinations of the invention provides valuable advantages for the treatment of HBV-induced diseases compared with monotherapy with the individual compounds, namely principally a synergistic antiviral activity, but also good tolerability of the combinations of the invention in Tox-50 (the range of toxicity at which 50% of the cells survive).

The substances referred to as HBV polymerase inhibitors B for the purposes of the invention are those which, in the endogenous polymerase assay which was published by Ph. A. Furman et al. in *Antimicrobial Agents and Chemotherapy*, Vol. 36 (No. 12), 2688 (1992) and which is described hereinafter, lead to an inhibition of the formation of an HBV DNA double strand, so as to result in a maximum of 50% of the activity of the zero value.

HBV polymerase inhibitors B for use in the invention are the substances disclosed in the endogenous polymerase experiment published in "Antimicrobial Agents and Chemotherapy" Vol. 36 (No. 12), 2688 (1992) by Ph. A. Furman, and the substances described below for inhibiting the formation of double-stranded HBV DNA thereby resulting in the maximum 50% activity value to be zero.

HBV virions from culture supernatants incorporate nucleoside 5'-triphosphates into the plus strand of the HBV DNA in vitro. By using agarose gel electrophoresis, the incorporation of $[\alpha\text{-}^{32}P]$-deoxynucleoside 5'-triphosphate into the viral 3.2 kb DNA product is observed in the presence and absence of a substance potentially having HBV polymerase-inhibiting properties. HBV virions are obtained from the cell culture supernatant of HepG2.2.15 cells by precipitation with polyethyleneglycol and are concentrated. One part by volume of clarified cell culture supernatant is mixed with ¼ by volume of an aqueous solution containing 50% by weight polyethylene glycol 8000 and 0.6 M sodium chloride. The virions are sedimented by centrifugation at 2500×g/15 minutes. The sediments are resuspended in 2 ml of buffer containing 0.05 M tris-HCl (pH 7.5) and dialyzed against the same buffer containing 100 mM potassium chloride. The samples can be frozen at −80° C. Each reaction mixture (100 µl) contains at least 105 HBV virions; 50 mM tris-HCl (pH 7.5); 300 mM potassium chloride; 50 mM magnesium chloride; 0.1% Nonident® P-40 (nonionic detergent from Boehringer Mannheim); 10 µM dATP, 10 µM dGTP, 10 µM dTTP; 10 µCi [$^{32}P$]dCTP (3000 Ci/mmol; final concentration 33 nM) and 1 µM of the potential polymerase inhibitor in its triphosphorylated form. The samples are incubated at 37° C. for one hour and then the reaction is stopped by adding 50 mM EDTA. A 10% weight/volume SDS solution (containing 10 g of SDS per 90 ml of water) is added to a final concentration of 1% by volume (based on the total volume), and proteinase K is added to a final concentration of 1 mg/ml. After incubation at 37° C. for one hour, samples are extracted with the same volume of phenol/chloroform/isoamyl alcohol (ratio 25:24:1 by volume), and the DNA is precipitated from the aqueous phase with ethanol. The DNA pellet is resuspended in 10 µl of gel buffer (solution of 10.8 g of tris, 5.5 g of boric acid and 0.75 g of EDTA in 1 liter of water (=TBE buffer)) and separated by electrophoresis in an agarose gel. Either the gel is dried or the nucleic acids present therein transferred by the Southern transfer technique to a membrane. The amount of labeled DNA double strand formed is then determined in relation to the negative control (=endo-pol reaction without substance or with inactive control substance). An HBV polymerase inhibitor is present if a maximum of 50% of the activity of the negative control is present.

Preferred HBV polymerase inhibitors B) comprise, for example, 3TC=lamivudine=4-amino-1-[(2R-cis)-2-(hydroxymethyl)-1,3-oxathiolan-5-yl-]-pyrimidin-2(1H)-one, cf. EP-B 382 526 (=U.S. Pat. No. 5,047,407) and WO 91/11186 (=U.S. Pat. No. 5,204,466); Adefovir dipivoxil=9-{2-[[bis[(pivaloyloxy)-methoxy]-phosphinyl]-methoxy]-ethyl}-a-denine, cf. EP-B 481 214 (=U.S. Pat. Nos. 5,663,159 and 5,792,756), U.S. Pat. Nos. 4,724,233 and 4,808,716; BMS 200475=[1S-(1-α,3-α,4-β)]-2-amino-1,9-dihydro-9-[4-hydroxy-3-(hydroxymethyl)-2-methylene-cyclopentyl]-6H-purin-6-one, cf. EP-B 481 754 (=U.S. Pat. Nos. 5,206,244 and 5,340,816), WO 98/09964 and 99/41275; Abacavir=(−)-(1S-cis)-4-[2-amino-6-(cyclopropylamino)-9H-purin-9-yl]-2-cyclopentene-1-methanol, cf. EP-B 349 242 (=U.S. Pat. No. 5,049,671) and EP-B 434 450 (=U.S. Pat. No. 5,034,394); FTC=(2R-cis)-4-amino-5-fluoro-1-[2-(hydroxymethyl)-1,3-oxathiolan-5-yl]-pyrimidin-2(1H)-one, cf. WO 92/14743 (=U.S. Pat. Nos. 5,204,466, 5,210,085, 5,539,116, 5,700,937, 5,728,575, 5,814,639, 5,827,727, 5,852,027, 5,892,025, 5,914,331, 5,914,400) and WO 92/18517; β-L-FDDC=5-(6-amino-2-fluoro-9H-purin-9-yl)-tetrahydro-2-furanmethanol, cf. WO 94/27616 (=U.S. Pat. Nos. 5,627,160, 5,561,120, 5,631,239 and 5,830,881); L-FMAU=1-(2-deoxy-2-fluoro-β-L-arabinofuranosyl)-5-methyl-pyrimidine-2,4(1H,3H)-dione, cf. WO 99/05157, WO 99/05158 and U.S. Pat. No. 5,753,789.

A further preferred embodiment of the invention relates to a composition comprising A) the above dihydropyrimidines having formula (I) and (Ia); and B) lamivudine.

Other preferred HBV antiviral agents B comprise, for example, phenylpropenamides of the following formula:

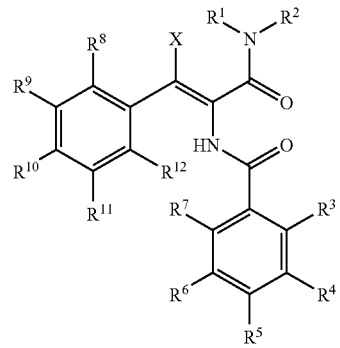

wherein $R^1$ and $R^2$ are, each independently, $C_{1-4}$ alkyl or, together with the nitrogen atom on which they are located, form a ring having 5 to 6 ring atoms which comprise carbon and/or oxygen; $R^3$ to $R^{12}$ are each independently hydrogen, halogen, $C_{1-4}$ alkyl, optionally substituted $C_{1-4}$ alkoxy, nitro, cyano or trifluoromethyl; and $R^{13}$ is hydrogen, $C_{1-4}$ alkyl, $C_{1-7}$ acyl or aralkyl and X is halogen or optionally substituted $C_{1-4}$ alkyl.

The phenylpropenamides and their preparation methods are disclosed in WO 98/33501, and are mentioned here for publication. AT-61 is the compound

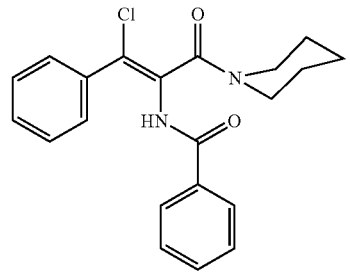

Preferred immunomodulators C) comprise, for example, all interferons such as α-, β- and γ-interferons, in particular also α-2a- and α-2b-interferons, interleukins such as interleukin-2, polypeptides such asthymosin-α-1 and thymoctonan, imidazoquinoline derivatives such as Levamisole®, immunoglobulins and therapeutic vaccines.

A further preferred embodiment of the invention relates to combinations of A) above dihydropyrimidines (I) and (Ia), B) lamivudine and, where appropriate, C) an interferon.

Description of Tests

The antiviral action of the compounds of the invention on hepatitis B virus is investigated by methods based on those described by M. A. Sells et al., *Proc. Natl. Acad. Sci.*, 84, 1005-1009 (1987) and B. E. Korba et al., *Antiviral Research* 19, 55-70 (1992).

The antiviral tests are carried out in 96-well microtiter plates. The first vertical row of the plate receives only growth medium and HepG2.2.15 cells. It serves as virus control.

Stock solutions of the test compounds (50 mM) are initially dissolved in DMSO, and further dilutions are prepared in the HepG2.2.15 growth medium. The compounds according to the invention are usually pipetted in a test concentration of 100 µM (1st test concentration) in each case into the second vertical test row of the microtiter plate and subsequently diluted in twofold steps 210 times in growth medium plus 2% by weight of fetal calf serum (volume 25 µl)

Each well of the microtiter plate then contains 225 µl of HepG2.2.15 cell suspension (5×104 cells/ml) in growth medium plus 2% by weight of fetal calf serum. The test mixture is incubated at 37° C. and 5% CO2 (v/v) for 4 days.

The supernatant is then aspirated off and discarded, and the wells receive 225 µl of freshly prepared growth medium. The compounds according to the invention are each added anew as 10-fold concentrated solution in a volume of 25 µl. The mixtures are incubated for a further 4 days Before harvesting the supernatants to determine the antiviral effect, the HepG2.2.15 cells are examined under the light microscope or by means of biochemical detection methods (for example Alamar Blue stain or Trypan Blue stain) for cytotoxic changes The supernatant and/or cells are then harvested and sucked by means of a vacuum onto 96-well dot-blot chambers covered with a nylon membrane (in accordance with the manufacturer's information).

Cytotoxicity Determination

Substance-induced cytotoxic or cytostatic changes in the HepG2.2.15 cells are detected, for example, under the light microscope as changes in cell morphology. Such substance-induced changes in the HepG2.2.15 cells compare with untreated cells are visible, for example, as cytolysis, vacuolation or altered cell morphology. A 50% cytotoxicity (Tox.-50) means that 50% of the cells show a morphology comparable to the corresponding cell control.

The tolerability of some of the compounds according to the invention is additionally tested on other host cells such as, for example, HeLa cells, primary human peripheral blood cells or transformed cell lines such as H-9 cells.

No cytotoxic changes are detectable at concentrations >10 µM of the compounds of the invention.

Determination of the Antiviral Action

After the supernatants or lysed cells is transferred to the nylon membrane of the blot apparatus (see above), the intra- or extracellular supernatants of the HepG2.2.15 cells are denatured (1.5 M NaCl/0.5 N NaOH), neutralized (3 M NaCl/0.5M Tris HCl, pH 7.5) and washed (2×SSC). The DNA is then baked onto the membrane by incubating the filters at 120° C. for 2-4 hours.

DNA Hybridization

Detection of the viral DNA from the treated HepG2.2.15 cells on the nylon filters is usually carried out with nonradioactive, digoxigenin-labeled hepatitis B-specific DNA probes, each of which is labeled with digoxigenin, purified and employed for the hybridization in accordance with the manufacturer's information.

The prehybridization and hybridization take place in 5×SSC, 1× blocking reagent, 0.1% by weight N-lauroylsarcosine, 0.02% by weight SDS and 100 µg of herring sperm DNA. The prehybridization takes place at 60° C. for 30 minutes, and the specific hybridization takes place with 20 to 40 ng/ml of the digoxigenized, denatured HBV-specific DNA (14 hours, 60° C.). The filters are then washed.

Detection of HBV-DNA by Digoxigenin Antibodies

The immunological detection of the digoxigenin-labeled DNA took place in accordance with the manufacturer's information:

The filters were washed and prehybridized in a blocking reagent (in accordance with the manufacturer's information). Hybridization was then carried out with an anti-DIG antibody coupled to alkaline phosphatase for 30 minutes. After a washing step, the substrate of alkaline phosphatase, CSPD, was added, incubated with the filters for 5 minutes, then packed in plastic film and incubated at 37° C. for a further 15 minutes. The chemiluminescence of the hepatitis B-specific DNA signals was visualized by exposing the filters to an X-ray film (incubation depending on signal strength: 10 minutes to 2 hours).

The half-maximum inhibitory concentration ($IC_{50}$, 50% inhibitory concentration) was determined as the concentration at which the intra- or extracellular hepatitis B-specific band was reduced by the compound according to the invention by 50% compared with an untreated sample.

It is unexpected that the compound of the invention exhibits an effective antiviral effect with an $IC_{50}$ less than 1 nM. Therefore, the compound of the invention is suitable for use in treating the diseases induced by viruses, especially acute and chronic persistent HBV infections. Chronic viral diseases induced by HBV can worsen the morbidity and the chronic hepatitis B virus infection can cause liver cirrhosis and/or hepatocellular carcinoma in many cases.

Areas of indication which may be mentioned for the compounds of the invention are, for example: the treatment of acute and chronic viral infections which may lead to infectious hepatitis, for example infections with hepatitis B viruses. The compounds of the invention are particularly suitable for the treatment of chronic hepatitis B infections and the treatment of acute and chronic hepatitis B viral infections.

The present invention includes pharmaceutical preparations which, besides nontoxic, inert pharmaceutically suitable carriers, comprise one or more compounds (I) or (Ia) or a combination of the invention or which consist of one or more active ingredients (I) or (Ia) or of a combination of the invention.

The active ingredients (I) and (Ia) are intended to be present in the pharmaceutical preparations mentioned above in a concentration of about 0.1 to 99.5% by weight, preferably of about 0.5 to 95% by weight, of the complete mixture.

The pharmaceutical preparations mentioned above may also comprise other active pharmaceutical ingredients apart from the compounds (I) and (Ia).

The ratio of the amounts of the components A, B and, where appropriate, C in the compositions of the invention may vary within wide limits; it is preferably 5 to 500 mg of A/10 to 1000 mg of B, in particular 10 to 200 mg of A/20 to 400 mg of B.

Component C, which is also to be used where appropriate, may be used in amounts of, preferably, 1 to 10 million, in particular 2 to 7 million, I.U. (international units), about three times a week over a period of up to one year.

The compounds or compositions of the invention are intended to be present in the pharmaceutical preparations mentioned above in general in a concentration of about 0.1 to 99.5, preferably about 0.5 to 95, % by weight of the complete mixture.

The pharmaceutical preparations mentioned above can be produced in a conventional way by known methods, for example by mixing the active ingredient(s) with the carrier(s).

It has generally proved to be advantageous both in human and in veterinary medicine to administer the active ingredient(s) in total amounts of about 0.5 to about 500, preferably of 1 to 100 mg/kg of body weight every 24 hours, where appropriate in the form of a plurality of single doses, to achieve the desired results. A single dose contains the active ingredient(s) preferably in amounts of about 1 to about 80, in particular 1 to 30 mg/kg of body weight. However, it may be necessary to deviate from the dosages mentioned, in particular depending on the species and body weight of the subject to be treated, the nature and severity of the disorder, the type of preparation and mode of administration of the medicament, and the time or interval within which administration takes place.

The invention therefore relates further to the compounds and compositions defined above for controlling diseases.

The invention further relates to medicaments comprising at least one of the compounds or compositions defined above and, where appropriate, one or more other active pharmaceutical ingredient(s).

The invention further relates to the use of the compounds and compositions defined above for producing a medicament for the treatment and prophylaxis of the diseases described above, preferably of viral diseases, in particular of hepatitis B.

The percentage data in the following examples relate in each case to weight unless indicated otherwise. The ratios of solvents in solvent mixtures are in each case based on volume.

EXAMPLES

A. Preparation of Intermediates

Intermediate 1

Ethyl 4-(2-bromo-4-fluorophenyl)-2-(thiazol-2-yl)-6-methyl-1,4-dihydropyrimidine-5-carboxylic ester

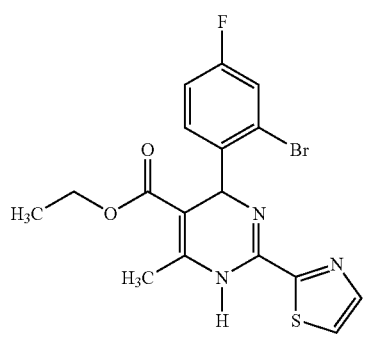

A mixture of 10.0 g (49.3 mmol) of 2-bromo-4-fluorobenzaldehyde, 6.4 g (49.3 mmol) of ethyl acetoacetate, 8.1 g (49.3 mmol) of 2-amidino-thiazole hydrochloride and 4.8 g (58.5 mmol) of sodium acetate was dissolved or suspended in 400 ml of ethanol and then boiled and refluxed for 16 hours. The solution obtained was cooled to room temperature and filtered. The residue was washed with water to remove inorganic salts. The product of 10.8 g (51.6%) was obtained. Melting point: 163-165° C.

Intermediate 2

Methyl 4-(2-bromo-4-fluorophenyl)-2-(thiazol-2-yl)-6-methyl-1,4-dihydropyrimidine-5-carboxylic ester Intermediate 2 was synthesized from methyl acetoacetate by a method similar to that for Intermediate 1. Yield: 53% (melting point: 155-157° C.).

Intermediate 3

Ethyl 6-bromomethyl-4-(2-bromo-4-fluorophenyl)-2-(thiazol-2-yl)-1,4-dihydropyrimidine-5-carboxylic ester

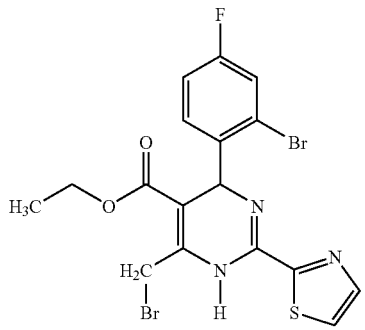

5.0 g (11.8 mmol) of Intermediate 1 was added into 100 ml of carbon tetrachloride and was heated to 50° C. in an atmosphere of the argon gas to obtain a clear solution. At this temperature, 2.33 g (13.0 mmol) of N-bromosuccinimide was added into the solution and mixed at the temperature for 10 minutes. The solution obtained was then cooled immediately and filtered at room temperature, and decompressed for concentration. The product obtained has a purity of higher than 90% according to the test result of HPLC, and was used as a raw material in the next step. Rf=0.69 (the ratio of petroleum ether to ethyl acetate is 8:2).

Intermediate 4

Methyl 6-bromomethyl-4-(2-bromo-4-fluorophenyl)-2-(thiazol-2-yl)-1,4-dihydropyrimidine-5-carboxylic ester Intermediate 4 was synthesized from Intermediate 2 by a method similar to that for the preparation of Intermediate 3. Rf=0.69 (the ratio of petroleum ether to ethyl acetate is 8:2).

B. Preparations of Examples

Example 5

Ethyl 4-(2-bromo-4-fluorophenyl)-2-(thiazol-2-yl)-6-(4-morpholinylmethyl)-1,4-dihydropyrimidine-5-carboxylic ester

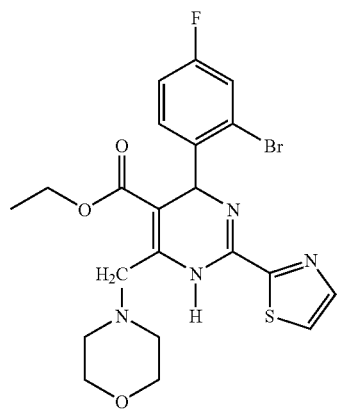

2.0 g of Intermediate 2 was added into 15 ml of methanol to form a solution. The solution was mixed with 5 times of morpholine and stirred for 30 minutes at room temperature. The solution obtained was then diluted with water and extracted with ethyl acetate. Yield: 1.7 g. Melting point: 161-163° C. Rf=0.45 (the ratio of petroleum ether to ethyl acetate is 8:2)

Example 6

Methyl 4-(2-bromo-4-fluorophenyl)-2-(thiazol-2-yl)-6-(4-morpholinylmethyl)-1,4-dihydropyrimidine-5-carboxylic ester

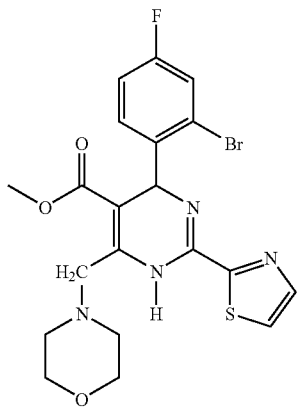

Example 6 was synthesized from Intermediate 4 by a method similar to that for the preparation of Example 5. Melting point: 173-175° C. Rf=0.43 (the ratio of petroleum ether to ethyl acetate is 8:2).

The enantiomers prepared in Example 5 and Example 6 were separated on a chiral column (Daicel Chiralpak AS-H, mobile phase: n-hexane/ethanol=99/1).

The anti-HBV active compounds in the two examples are enantiomers having a relatively long retention time.

The activity data of the compounds of the invention are listed below:

| Example No. | IC$_{50}$ (nM) |
| --- | --- |
| 5 | 0.2 |
| (—)-5 | 0.1 |
| 6 | 0.3 |
| (—)-6 | 0.2 |

The treatment of the hepatitis B virus-producing HepG2.2.15 cells with the compounds of the invention can lead to a reduction in intra- and/or extracellular viral DNA.

INDUSTRIAL APPLICABILITY

The examples disclosed herein show that the compounds disclosed herein exhibit an effective antiviral effect with the IC$_{50}$ less than 1 nM. Therefore, the compounds can be used for the treatment of a disease induced by viruses, especially acute and chronic persistent HBV infections according to the methods of the invention or any method known to a person skilled in the art.

What is claimed is:

1. A compound having formula (I) or its isomer (Ia):

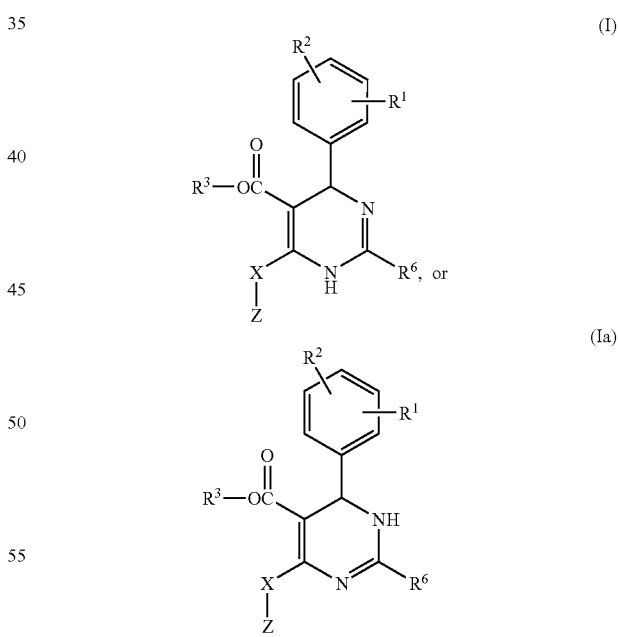

or an enantiomer or a salt thereof, wherein R$^1$ is o-bromine, R$^2$ is p-fluorine, R$^3$ is a C$_1$-C$_4$ alkyl, R$^6$ is thiazolyl-2-yl, X is methylene, and Z is morpholinyl.

2. The compound of claim 1 or the enantiomer or the salt thereof, wherein R$^1$ is o-bromine, R$^2$ is p-fluorine, R$^3$ is methyl or ethyl, R$^6$ is thiazolyl-2-yl, X is methylene, and Z is morpholinyl.

3. A compound having one of the following structures or an enantiomer, tautomer or salt thereof:

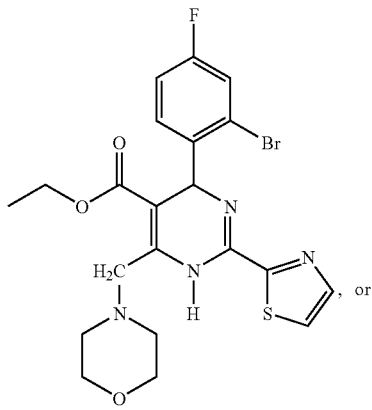, or

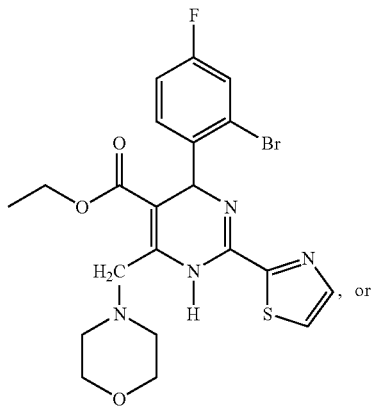

4. A compound having one of the following structures or a levo isomer, tautomer or salt thereof:

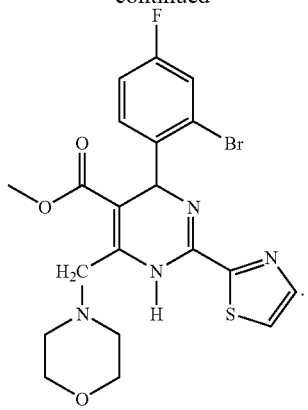, or

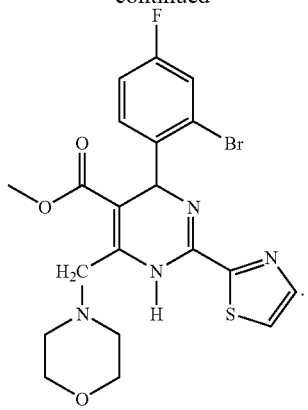

-continued

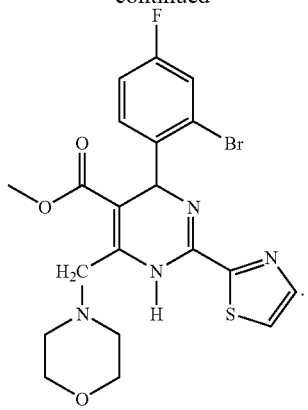.

5. The compound according to claim 1 or the enantiomer or the salt thereof, wherein the salt is an inorganic acid salt or an organic acid salt.

6. The compound according to claim 5 or the enantiomer or the salt thereof, wherein the inorganic acid salt is a hydrochloric acid salt, a hydrobromic acid salt, a phosphoric acid salt or a sulfuric acid salt.

7. The compound according to claim 5 or the enantiomer or the salt thereof, wherein the organic acid salt is a carboxylate or a sulfonate.

8. The compound according to claim 7 or the enantiomer or the salt thereof, wherein the carboxylate is acetate, maleate, fumarate, malate, citrate, tartarate, lactate or benzoate.

9. The compound according to claim 7 or the enantiomer or the salt thereof, wherein the sulfonate is methanesulfonate, ethanesulfonate, benzenesulfonate, toluenesulfonate or naphthalenedisulfonate.

10. A method of preparing the compound of claim 1, wherein the method is characterized by:

(a) reacting a benzaldehyde having formula (II) with a β-ketoester having formula (III) to produce a benzylidene compound having formula (IV):

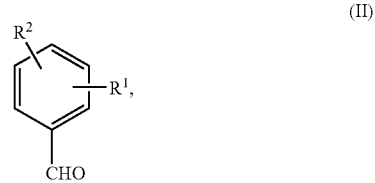

(II)

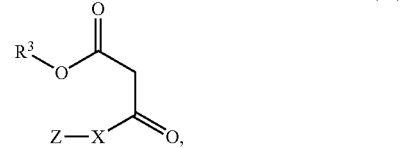

(III)

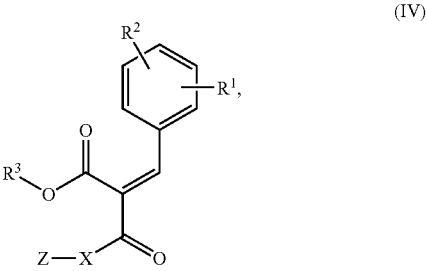

(IV)

and (b) reacting the benzylidene compound having formula (IV) with an amidine having formula (V):

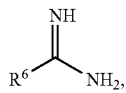
(V)

or a salt thereof
wherein $R^1$ is o-bromine, $R^2$ is p-fluorine, $R^3$ is a $C_1$-$C_4$ alkyl, $R^6$ is thiazolyl-2-yl, X is methylene, and Z is morpholinyl.

11. A method of preparing the compound of claim 1, wherein the method is characterized by reacting a compound having formula (III) with an aldehyde having formula (II) and an amidine having formula (V) or a salt thereof in one step,

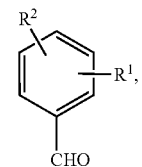
(II)

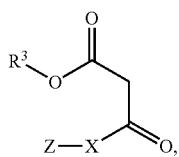
(III)

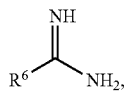
(V)

wherein $R^1$ is o-bromine, $R^2$ is p-fluorine, $R^3$ is a $C_1$-$C_4$ alkyl, $R^6$ is thiazolyl-2-yl, X is methylene, and Z is morpholinyl.

12. A method of preparing the compound of claim 1, wherein X of formula (I) is methylene and the method is characterized by reacting the compound having formula (VI) with morpholine (VII) or a salt thereof:

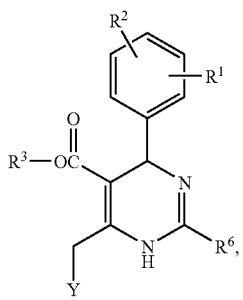
(VI)

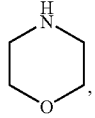
(VII)

wherein Y is a nucleophilic substituent, and $R^1$ is o-bromine, $R^2$ is p-fluorine, $R^3$ is a $C_1$-$C_4$ alkyl, and $R^6$ is thiazolyl-2-yl.

13. A method of preparing the compound of claim 1, which is characterized by the step of reacting a compound having formula (II) with an aldehyde having formula (X) and an amidine having formula (V) or a salt thereof:

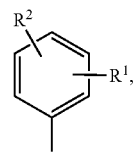
(II)

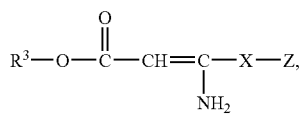
(X)

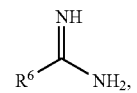
(V)

wherein $R^1$ is o-bromine, $R^2$ is p-fluorine, $R^3$ is a $C_1$-$C_4$ alkyl, $R^6$ is thiazolyl-2-yl, X is methylene, and Z is morpholinyl.

14. A composition comprising the following components:
A) at least one compound according to claim 1;
B) at least an HBV antiviral agent which is different from component A; and, when appropriate,
C) at least an immunomodulator or an interferon.

15. The composition of claim 14, wherein the component B is an HBV polymerase inhibitor, lamivudine or a phenylpropenamide compound having the following formula:

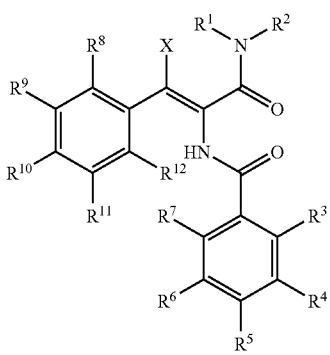

or a salt thereof, wherein
each of $R^1$ and $R^2$ is independently $C_{1-4}$ alkyl or, together with the nitrogen atom on which they are located, form a ring having 5 to 6 ring atoms which comprise carbon and/or oxygen; and each of $R^3$ to $R^{12}$ is independently hydrogen, halogen, $C_1$-$C_4$-alkyl, optionally substituted $C_1$-$C_4$-alkoxy, nitro, cyano or trifluoromethyl.

16. The composition of claim 15, wherein the component B is the phenylpropenamide compound having the following structure:

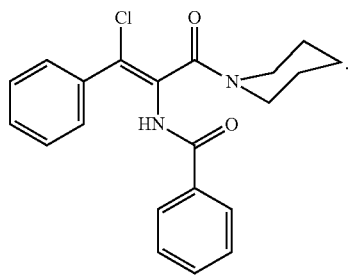

17. A medicament comprising at least one composition of claim 14, and, when appropriate, one or more active pharmaceutical agents.

18. A method for treating hepatitis B infection or a disease caused by hepatitis B infection, which comprises administering the composition of claim 14 to a patient having the disease.

19. The method of claim 18, wherein the method is for treating the disease caused by hepatitis B infection selected from hepatitis, cirrhosis or hepatocellular carcinoma.

20. A method for treating hepatitis B infection or a disease caused by hepatitis B infection, which comprises administering the compound of claim 1 to a patient having the disease.

21. The method of claim 20, wherein the method is for treating the disease caused by hepatitis B infection selected from hepatitis, cirrhosis or hepatocellular carcinoma.

22. A pharmaceutical composition comprising at least one compound according to claim 1, and, when appropriate, a pharmaceutically acceptable carrier.

* * * * *